US 6,720,441 B2

(12) United States Patent
Forbert et al.

(10) Patent No.: US 6,720,441 B2
(45) Date of Patent: Apr. 13, 2004

(54) RECOVERY AND PURIFICATION OF SUBSTITUTED BENZENESULFONATES

(75) Inventors: Rainald Forbert, Floersheim (DE); Thomas Diehl, Floersheim (DE)

(73) Assignee: Siemens Axiva GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 10/153,908

(22) Filed: May 24, 2002

(65) Prior Publication Data

US 2002/0193628 A1 Dec. 19, 2002

Related U.S. Application Data

(63) Continuation of application No. PCT/EP00/11223, filed on Nov. 14, 2000.

(30) Foreign Application Priority Data

Nov. 25, 1999 (DE) .......................................... 199 56 862

(51) Int. Cl.$^7$ .............................................. C07C 302/00
(52) U.S. Cl. .......................................... 558/44; 558/45
(58) Field of Search ..................... 558/44, 45

(56) References Cited

U.S. PATENT DOCUMENTS

| 2,847,459 A | 8/1958 | Mitchell |
| 4,321,214 A | 3/1982 | Nicolet |
| 4,690,785 A | 9/1987 | Mausner et al. |

FOREIGN PATENT DOCUMENTS

| DE | 11 31 662 B | 6/1962 |
| DE | 33 37 921 A1 | 5/1985 |
| EP | 0 922 694 A2 | 6/1999 |
| EP | 0 922 695 A1 | 6/1999 |
| WO | WO 95/07882 | 3/1995 |
| WO | WO 96/28417 | 9/1996 |
| WO | WO 99/09004 | 2/1999 |

OTHER PUBLICATIONS

Kurt Kosswig, "Surfactants" in: Ullmann's Encyclopedia of Industrial Chemistry, vol. A 25, 1994, VCH Verlagsgesellschaft mbH, pp. 747–817.

Martin Zogg, Einführung in die Mechanische Verfahrenstechnik,–3$^{rd}$ ed.., Stuttgart: B.G. Teubner, 1993, pp. 15–17.

Peter Walzel, Zerstäuben von Flüssigkeiten, Chem.–Ing.–Tech. vol. 62, No. 12 (1990), VCH Verlagsgesellschaft mbH, pp. 983–994.

Peter Walzel, "Spraying and Atomizing of Liquids" in: Ullmann's Encyclopedia of Industrial Chemistry, vol. B2, 1988, VCH Verlagsgesellschaft mbH, pp. 6–1 to 6–14.

*Primary Examiner*—Paul J. Killos
(74) *Attorney, Agent, or Firm*—Sughrue Mion, PLLC

(57) ABSTRACT

A process for recovering and purifying substituted benzenesulfonates, by neutralizing a mixture including at least one substituted benzenesulfonate, or at least one corresponding substituted benzenesulfonic acid, and sulfur trioxide, sulfuric acid and/or hydrogen chloride in free or bound form, in an aqueous phase using an alkali metal hydroxide, and purifying it in this aqueous phase, and by subsequently separating the substituted benzenesulfonate(s) from this aqueous phase. The mixture is comminuted into particles having a Sauter mean diameter in the range from 1 $\mu$m to 2 cm, either before or during introduction into this aqueous phase.

29 Claims, No Drawings

RECOVERY AND PURIFICATION OF SUBSTITUTED BENZENESULFONATES

This is a Continuation of International Application PCT/EP00/11223, with an international filing date of Nov. 14, 2000, which was published under PCT Article 21(2) in German, and the disclosure of which is incorporated into this application by reference.

FIELD OF AND BACKGROUND OF THE INVENTION

The invention relates to a process for recovering and purifying substituted benzenesulfonates, by neutralizing a mixture comprising at least one substituted benzenesulfonate or at least one corresponding substituted benzenesulfonic acid, sulfur trioxide, sulfuric acid and/or hydrogen chloride in free or bound form, in an aqueous phase using an alkali metal hydroxide, and purifying it in this aqueous phase, and by subsequently separating said substituted benzenesulfonate(s) from this aqueous phase.

Substituted benzenesulfonates have a wide range of application. Alkylbenzenesulfonates having more than 5 carbon atoms in the alkyl group are the most commonly used nonsoap surfactants, since they possess good cleaning, emulsifying, foam-forming and wetting properties. Linear alkylbenzenesulfonates possess good biodegradability and are therefore an essential constituent of many laundry detergents and other cleaning agents. Amido acid phenyl ester sulfonates serve as bleach activators in laundry detergents and other cleaning agents which contain bleach. These activators have a number of advantageous properties, such as excellent bleaching performance combined with minimal damage to fabric dyes, good compatibility with washing machines and a good odor profile in laundering.

The prior art discloses many different synthetic routes to substituted benzenesulfonates.

It is known ["Surfactants" in Ullmann's Encyclopedia of Industrial Chemistry, Vol. A25, p. 747–817, Weinheim 1994, and DE-A 1 131 662] that surface-active alkylbenzenesulfonates can be obtained by sulfonating alkylbenzenes having a side chain containing from 8 to 20 carbon atoms using oleum, removing the excess sulfuric acid and then neutralizing the reaction product using sodium hydroxide. However, the products obtained in this way contain from 10 to 15% of extraneous salts after neutralization, which consist essentially of sodium sulfate, stemming from the excess sulfonating agent, and also from a small amount of sodium chloride, which stems from the bleaching process using sodium hypochlorite that optionally follows the neutralization.

The alkylbenzenesulfonate is freed of these organic salts by known methods involving extraction by organic solvents, such as alcohols or also chlorinated hydrocarbons. However, these processes are laborious and do not always give the required results.

From "Surfactants" in Ullmann's Encyclopedia of Industrial Chemistry, Vol. A25, p. 747–817, Weinheim 1994, it is further known that sulfonation can be carried out with pure sulfur trioxide, by which means the occurrence of extraneous salts during neutralization is reduced. The sulfonation process using sulfur trioxide in gaseous or liquid form is, however, complicated in view of the apparatus required. Furthermore, the sodium alkylbenzenesulfonates obtained from this process contain a content of extraneous salts (sodium sulfate, sodium chloride) in the percent range based on the active substance.

Furthermore, it is known that chlorosulfonic acid can be used as a sulfonating agent. This method can lead to the partial formation of alkylbenzenesulfonyl chlorides, which lead to the formation of sodium chloride and sodium sulfate as by-products during further processing.

Furthermore, it is known that sodium alkylbenzenesulfonate can be salted out of aqueous solutions, which may also contain dissolved sodium sulfate, using sodium chloride. However, it has been shown that alkylbenzenesulfonates containing low extraneous salt levels are not obtained by this method until after long settling times, and still contain a certain content of sodium sulfate. Therefore, these products cannot be used in the preparation of cosmetic products sensitive to sodium sulfate, or as emulsifiers in industrial scale processes which take place in the emulsion phase.

DE-A 1 131 662 discloses that alkylbenzenesulfonates can be salted out using a mixture which comprises a content of alkylpolysulfonates as well as sodium chloride and sodium sulfate, and that the layer separation between aqueous phase and alkylbenzenesulfonate-rich phase is achieved more quickly as a result, after which the alkylbenzenesulfonates containing low extraneous salt contents are obtained as an aqueous paste and can be separated from the lower layer by known methods. This process has the disadvantage first that the alkylpolysulfonates used end up as undesirable constituents in the product, and secondly that they pollute the wastewater from the process. Also, the settling times required for this process are several hours.

Furthermore, various synthetic routes to amido acid phenyl ester sulfonates are known from the prior art as represented in, for example, WO 95/07882, WO 96/28417, EP 0 922 694 and EP 0 922 695. WO 99/09004 discloses a process for the preparation and purification of amido acid phenyl ester sulfonates.

All the above-described processes for recovery and purification of substituted benzenesulfonates, in particular p-substituted benzenesulfonates, have the problem in common that the substituted benzenesulfonates after operation of the described processes are obtained in consistencies ranging from pastelike to gellike in the presence of water and/or of solvents, so that the substituted benzenesulfonates can only be separated out of the synthesis and/or purification mixtures very slowly and without satisfactory purity. The consequences are uneconomically large separating apparatus and undesirably high product contamination by by-products, such as extraneous salts, or yield losses when washes and/or bleaches are used ["Surfactants" in Ullmann's Encyclopedia of Industrial Chemistry, Vol. A25, p. 747+817, Weinheim 1994, and DE-A 1 131 662].

OBJECTS OF THE INVENTION

It is an object of the present invention to provide a process for the recovery and purification of substituted benzenesulfonates that first does not have the disadvantage of very slow mechanical separation of the product, and secondly achieves satisfactorily high purities.

SUMMARY OF THE INVENTION

We have found that this object is achieved by a process for recovering and purifying substituted benzenesulfonates by neutralizing a mixture comprising at least one substituted benzenesulfonate, or at least one corresponding substituted benzenesulfonic acid, and sulfur trioxide, sulfuric acid and/or hydrogen chloride in free or bound form, in an aqueous phase using an alkali metal hydroxide, and purifying it in this aqueous phase, and by subsequently separating said substituted benzenesulfonate(s) from this aqueous phase, wherein said mixture is comminuted into particles having a Sauter mean diameter in the range from 1 μm to 2 cm, either before or during introduction into this aqueous phase.

For the purposes of this invention, "neutralization" and related words such as "neutralize" relate quite generally to the neutralization reaction: base+acid=salt+water, and not necessarily to the specific definition of setting to neutral, which is associated with a pH value of about 7.

Particle swarms in most cases do not consist of unitary particles of equal size.

Characterization of the particle size of a particle swarm is carried out in this invention by means of the Sauter mean diameter, since it is decisive in process separating operations using particles subjected to flow, such as filtration. The Sauter mean diameter of a particle swarm is calculated from the volume Vp and the surface area A of all particles of a swarm by the formula: 6Vp/A, see M. Zogg, "Einführung in die mechanische Verfahrenstechnik", pp. 15–17, Stuttgart 1993.

DETAILED DESCRIPTION OF THE PREFERRED EMBODIMENTS

For the purposes of this invention, substituted benzenesulfonates have the general structural formula:

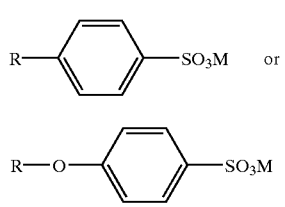

in which the two substituents on the benzene ring can be in the para-arrangement shown, or else in the meta- or ortho-arrangement. The two substituents on the benzene ring are preferably in the para-arrangement shown. R is a linear or branched alkyl or alkylene group having from 3 to 20 carbon atoms, which can first be interrupted by at least one O and/or NH group, and secondly can be substituted by at least one oxo group. M is an alkali metal, preferably sodium.

Particularly preferred substituted benzenesulfonates are linear sodium alkylbenzenesulfonates having from 8 to 16 carbon atoms in the alkyl group, and also 4-sulfophenyl[(1-oxyalkanoyl)amino]alkanoates.

A very particularly preferred substituted benzenesulfonate is sodium n-nonanoylamidohexanoyl-oxybenzenesulfonate.

A preferred embodiment comprises comminuting the mixture into particles, having a Sauter mean diameter in the range from 10 μm to 0.5 cm, preferably from 20 μm to 1000 μm, more preferably from 25 μm to 300 μm, most preferably from 30 μm to 100 μm.

The mixture preferably comprises from 0.1 to 20%, more preferably from 1 to 15%, most preferably from 2 to 10% of sulfur trioxide, sulfuric acid and/or hydrogen chloride in free or bound form.

The mixture may include further components such as by-products, solvent and catalysts.

Comminution of the mixture into particles can be carried out by all processes known to the person skilled in the art for this purpose, for example jetting, e.g., sonic, ultrasonic, and sinusoidal waves, laminar jet disintegration and dripping, as are described, for example, in P.Walzel, "Zerstäuben von Fl üssigkeiten", Chem.-Ing.-Tech. 62 (1990) No., 12, pp. 983–994 and "Spraying and Atomizing of Liquids" in Ullmann's encyclopedia of industrial chemistry, Vol. B2, pp. 6-1–6-14, Weinheim 1988). The mixture is preferably atomized above the surface area of the aqueous phase before introduction into it, more preferably by using at least one one-material nozzle.

In a particular embodiment of the process, the comminution is preceded by the removal from the mixture of any relatively large particles which could block the device carrying out comminution of the mixture into particles by means of at least one magnetic precipitator and/or at least one screen and/or at least one filter and/or at least one wet grinding machine and/or at least one homogenizing machine.

The pH of the aqueous phase in which the mixture is neutralized and purified is preferably held in the range from 7 to 9, more preferably from 7.5 to 8.5, by addition of the alkali metal hydroxide.

The temperature of the aqueous phase in which the mixture is neutralized and purified is preferably held in the range from 0° C. to 80° C., more preferably from 10° C. to 50° C., most preferably from 20° C. to 40° C., by direct or indirect cooling.

In a preferred embodiment of the process, the aqueous phase in which the mixture is neutralized and purified is mixed using at least one mixing device having circumferential velocities in the range from 0.05 to 5 m/s, preferably from 0.1 to 1 m/s, more preferably from 0.2 to 0.5 m/s.

The separation of the substituted benzenesulfonate from the aqueous phase in which the mixture is neutralized and purified can be carried out by all processes that are known to the person skilled in the art for this purpose, for example sedimentation, filtration or centrifugation. The substituted benzenesulfonate is separated from the aqueous phase by vacuum filtration.

In a particular embodiment of the process, a portion of the separated aqueous phase is reused for the neutralization and purification of the mixture.

During or after separation of the substituted benzenesulfonate from the aqueous phase in which the mixture is neutralized and purified, the substituted benzenesulfonate can be washed with a washing system. The washing system preferably comprises more than 60% by weight of water.

In a particular embodiment of the process, the washing system is reused in its entirety or in portions as a washing system and/or is fed into the aqueous phase for neutralization and purification of the mixture after it is separated from the washed substituted benzenesulfonate.

The substituted benzenesulfonate may be dried for further purification after separation from the aqueous phase. All processes known to the person skilled in the art for this purpose can be used.

The process can be operated completely or partially batchwise or continuously, but is preferably carried out completely continuously.

The invention is based on, inter alia, the surprising effect of the separation of a substituted benzenesulfonate from the aqueous phase being effected much more quickly and with a much better separation, i.e., a higher purity, when the mixture comprising the substituted benzenesulfonate or the corresponding substituted benzenesulfonic acid is fed into the aqueous phase used for neutralization and purification in the form of particles which in view of their particle size and shape would themselves be easily removable, although the feed mixture itself is liquid.

The advantages of the process of the invention are essentially that a substituted benzenesulfonate is recovered in high purity and good yield using minimal apparatus and energy.

The above description of the preferred embodiments has been given by way of example. From the disclosure given, those skilled in the art will not only understand the present invention and its attendant advantages, but will also find apparent various changes and modifications to the and methods disclosed. It is sought, therefore, to cover all such changes and modifications as fall within the spirit and scope of the invention, as defined by the appended claims, and equivalents thereof.

What is claimed is:

1. A process for recovering and purifying substituted benzenesulfonates comprising:
   (a) comminuting a mixture comprising at least
      (1) a substituted benzene sulfonate or a substituted benzenesulfonic acid; and
      (2) at least one compound selected from the group consisting of sulfur trioxide, sulfuric acid and hydrogen chloride, any of which occurring in either free or bound form, into particles having a Sauter mean diameter in the range from 1 $\mu$m to 2 cm;
   (b) neutralizing the mixture with an alkali metal hydroxide; and
   (c) separating the substituted benzenesulfonates.

2. The process as claimed in claim 1, wherein the mixture is purified after neutralization.

3. The process as claimed in claim 1, wherein the mixture is comminuted into particles having a Sauter mean diameter is in the range from 10 $\mu$m to 0.5 cm.

4. The process as claimed in claim 1, wherein the mixture comprises from 0.1 to 20% of at least one compound selected from the group consisting of sulfur trioxide, sulfuric acid and hydrogen chloride in free or bound form.

5. The process of claim 1, wherein the comminution is carried out by means of jetting, waves, laminar jet disintegration or dripping.

6. The process of claim 1, wherein the comminution is carried out by jetting using a one-material nozzle.

7. The process of claim 1, wherein the comminution is preceded by removal from the mixture of particles which could block the device carrying out the comminution of the mixture into particles by at least one means selected from the group consisting of a magnetic precipitator, at least one screen, at least one filter, at least one wet grinding machine, and at least one homogenizing machine.

8. The process of claim 1, wherein the pH of an aqueous phase, in which the mixture is neutralized, is held in a range from 7 to 9 by addition of the alkali metal hydroxide.

9. The process of claim 1, wherein the temperature of an aqueous phase in which the mixture is neutralized, is held in a range from 0° C. to 80° C. by direct or indirect cooling.

10. The process of claim 1, wherein an aqueous phase in which the mixture is neutralized, is mixed using at least one mixing device having circumferential velocities in the range from 0.05 to 5 m/s.

11. The process of claim 1, wherein the separation of the substituted benzenesulfonate is carried out by at least one of sedimentation, filtration or centrifugation, preferably by vacuum filtration out of the aqueous phase.

12. The process of claim 1, wherein a portion of the separated aqueous phase is reused for the neutralization of the mixture.

13. The process of claim 1, wherein the substituted benzenesulfonate is washed with a washing system during or after the separation of the substituted benzenesulfonate from the aqueous phase in which the mixture is neutralized.

14. The process of claim 12, wherein the washing system comprises at least 60% by weight water.

15. The process of claim 12, wherein a portion of the washing system is reused as a washing system or fed into the aqueous phase for neutralization of the mixture.

16. The process of claim 1, wherein the substituted denzenesulfonate is dried after it is separated.

17. A process for recovering and purifying substituted benzenesulfonates comprising:
   (a) providing a means for comminuting a mixture comprising at least
      (1) a substituted benzene sulfonate or a substituted benzenesulfonic acid; and
      (2) at least one compound selected from the group consisting of sulfur trioxide, sulfuric acid and hydrogen chloride, any of which occurring in either free or bound form, into particles having a Sauter mean diameter in the range from 1 $\mu$m to 2 cm;
   (b) neutralizing the mixture with an alkali metal hydroxide; and
   (c) separating the substituted benzenesulfonates.

18. A process for recovering and purifying substituted benzenesulfonates comprising:
   (a) comminuting a mixture comprising at least
      (1) a substituted benzene sulfonate or a substituted benzenesulfonic acid; and
      (2) at least one compound selected from the group consisting of sulfur trioxide, sulfuric acid and hydrogen chloride, any of which occurring in either free or bound form, into particles having a Sauter mean diameter in the range from 1 $\mu$m to 2 cm;
   (b) subsequently neutralizing the comminuted mixture with an alkali metal hydroxide in an aqueous phase;
   (c) purifying the substituted benzene sulfonates; and
   (d) separating substituted benzenesulfonates from the aqueous phase.

19. The process as claimed in claim 18, wherein the mixture is comminuted into particles having a Sauter mean diameter is in the range from 10 μm to 0.5 cm.

20. The process as claimed in claim 18, wherein the mixture comprises from 0.1 to 20% of at least one compound selected from the group consisting of sulfur trioxide, sulfuric acid and hydrogen chloride in free or bound form.

21. The process of claim 18, wherein the comminution is carried out by means of jetting, waves, laminar jet disintegration or dripping.

22. The process of claim 18, wherein the comminution is carried out by jetting using a one-material nozzle.

23. The process of claim 18, wherein the comminution is preceded by removal from the mixture of particles which could block the device carrying out the comminution of the mixture into particles by at least one means selected from the group consisting of a magnetic precipitator, at least one screen, at least one filter, at least one wet grinding machine, and at least one homogenizing machine.

24. The process of claim 18, wherein the pH of an aqueous phase, in which the mixture is neutralized and purified, is held in a range from 7 to 9 by addition of the alkali metal hydroxide.

25. The process of claim 18, wherein the temperature of an aqueous phase in which the mixture is neutralized and purified, is held in a range from 0° C. to 80° C. by direct or indirect cooling.

26. The process of claim 18, wherein an aqueous phase in which the mixture is neutralized and purified, is mixed using at least one mixing device having circumferential velocities in the range from 0.05 to 5 m/s.

27. The process of claim 18, wherein the separation of the substituted benzenesulfonate from the aqueous phase in which the mixture is neutralized and purified is carried out by at least one of sedimentation, filtration or centrifugation, preferably by vacuum filtration out of the aqueous phase.

28. The process of claim 18, wherein a portion of the separated aqueous phase is reused for the neutralization and purification of the mixture.

29. The process of claim 18, wherein the substituted benzenesulfonate is washed with a washing system during or after the separation of the substituted benzenesulfonate from the aqueous phase in which the mixture is neutralized and purified.

* * * * *